US008119374B2

(12) United States Patent
Peters-Wendisch et al.

(10) Patent No.: US 8,119,374 B2
(45) Date of Patent: Feb. 21, 2012

(54) NUCLEOTIDE SEQUENCES OF CORYNEFORM BACTERIA CODED FOR PROTEINS PARTICIPATING IN L-SERINE METABOLISM AND METHOD FOR MICROBIAL PRODUCTION OF L-SERINE

(75) Inventors: Petra Peters-Wendisch, Jülich (DE); Roman Netzer, Jülich (DE); Lothar Eggeling, Jülich (DE); Hermann Sahm, Jülich (DE)

(73) Assignee: Forschungszentrum Julich GmbH, Julich (DE)

( * ) Notice: Subject to any disclaimer, the term of this patent is extended or adjusted under 35 U.S.C. 154(b) by 825 days.

(21) Appl. No.: 12/136,190

(22) Filed: Jun. 10, 2008

(65) Prior Publication Data

US 2009/0061482 A1 Mar. 5, 2009

Related U.S. Application Data

(62) Division of application No. 10/549,262, filed on May 10, 2006.

(30) Foreign Application Priority Data

Mar. 13, 2003 (DE) .................................. 103 11 399

(51) Int. Cl.
*C12P 13/06* (2006.01)
*C12P 21/06* (2006.01)
*C12N 9/88* (2006.01)

(52) U.S. Cl. ......................... 435/116; 435/69.1; 435/232
(58) Field of Classification Search .......................... None
See application file for complete search history.

(56) References Cited

U.S. PATENT DOCUMENTS

| | | | |
|---|---|---|---|
| 6,037,154 A | 3/2000 | Suga | |
| 6,258,573 B1 | 7/2001 | Suga | |
| 2002/0197605 A1* | 12/2002 | Nakagawa et al. | ................ 435/6 |

FOREIGN PATENT DOCUMENTS

| EP | 0 149 539 A3 | 7/1985 |
|---|---|---|
| EP | 0 931 833 A2 | 7/1999 |

OTHER PUBLICATIONS

A. Schwarzer et al; Manipulation of Corynebacterium . . . ; Bio/Technology; vol. 9; Jan. 1991.
S. Moore et al; Chromatography of amino acids . . . ; The Rockefeller Institute for Med. Research; vol. 30, No. 7; Jul. 1958.
M. Tsuchiya et al; Genetic control systems of *escherichia* . . . ; Bio/Technology; vol. 6, Apr. 1988.
E. Radmacher et al; Linking central metabolism with . . . ; Applied and Environmental Microbiology, May 2002; 2246-2250.
A. Tauch et al; Efficient electrotransformation . . . ; Current Microbiology; vol. 45 (2002), pp. 362-367.
X. Zhang et al; Deficiency in L-Serine deaminase results . . . ; Molecular Microbiology (2008); 69(4); pp. 870-881.
S. Nakagawa; L-serine deaminase; NCBI; BAB99038; Jun. 2002.
M. Stolz et al; Reduced folate supply as a . . . ; Applied and Environmental Microbiology; Feb. 2007, pp. 750-755.
E. Boeggeman et al; Expression of deletion constructs . . . ; Protein Eng.; Sep. 1993; vol. 6, No. 7; pp. 779-785.
P.F. Yan et al; The role of COOH . . . ; Journ. Biol. Chem.; vol. 268; No. 30; Oct. 1993; pp. 22444-22449.
J. Labarre et al; Gene replacement, integration . . . ; Jour. Of Bacteriology, Feb. 1993, p. 1001-1007.
W. Liebl et al; Transfer of *brevibacterium*. . . ; Int. Jour. Of Systematic Bacteriology, Apr. 1991, p. 255-260.
P. Lindroth et al; High performance liquid chromatographic . . . ; Analytical Chemistry, vol. 51, Sep. 1979.
J.F. Martin et al; Cloning systems in amino . . . ; Bio/Tech. vol. 5, Feb. 1987; www.nature.com/naturebiotechnology.
E.Menkel et al; Influence of increased aspartate . . . ; Applied and Environmental Microbiology, Mar. 1989, 684-688.
S. Ohmori et al; Fluorimetric and high-performance . . . ; Jour. Of Chromatography, 566 (1991) 1-8.
P. Peters-Wendisch et al; 3-phosphoglycerate . . . ; Appl Microbiol Biotechnol (2002) 60: 437-441.
D.J. Reinscheid et al; Stable expression of hom-1-thrB . . . ; Applied and Environmental Microbiology, Jan. 1994, 126-132.
A. Schaefer et al; Small mobilizable multi-purpose . . . ; Gene, 145 (1994) 69-73.
A.Hofmeister et al; Cloning and Expression of Two Genes . . . ; Journal of Bacteriology; Aug. 1997; p. 4937-4941; vol. 179.
K.Kubota; Improved Production of L-Serine . . . ; Agric. Biol. Chem., 49 (1); 1985; XP-002287205.
A. Link et al; Methods for Generating Precise Deletions . . . ; Journal of Bacteriology; Oct. 1997; p. 6228-6237; vol. 179.
M.Bradford; A Rapid and Sensitive Method for . . . ; Analytical Biochemistry 72, 248-254 (1976).
B.Eikmanns et al; A family of *Corynebacterium glutamicum* . . . ; Gene. 102 (1991) 93-98.
S.G.N. Grant et al; Differential plasmid rescue from . . . ; Proc. Natl. Acad. Sci. USA; vol. 87, pp. 4645-4649; Jun. 1990.
C. Guerrero et al; Directed mutagenesis of a regulatory palindromic sequence . . . ; Gene, 138 (1994) 35-41.
A.E.M. Hofmeister et al; Iron-sulfur cluster-containing L-serine . . . ; FEBS Letters 351 (1994) 416-418.
Y.Izumi et al; L-Serine production by a methylotroph . . . ; Appl Microbiol Biotechnol (1993) 39: 427-432.
M. Jakoby et al; Construction and application of new . . . ; Biotechnology Techniques 13: 437-441, 1999.
W. Jaeger et al; Expression of the *Bacillus subtilis* . . . ; Jour. Of Bacteriology, Aug. 1992, p. 5462-5465.
B. Jones et al; *o-Phthaldialdehyde*precolumn derivatization . . . ; Journ. Of Chromatography, 266 (1983) 471 - 482.
C. Keilhauer et al; Isoleucine Synthesis in *corynebacterium*. . . ; Journ. Of Bacteriology, Sep. 1993, p. 5595-5603.

(Continued)

*Primary Examiner* — Tekchand Saidha
*Assistant Examiner* — Md. Younus Meah
(74) *Attorney, Agent, or Firm* — Jonathan Myers; Andrew Wilford (57) ABSTRACT

This invention relates to the nucleotide sequence of coryneform bacteria coding for proteins which are involved in L-serine metabolism with reduced and switched off L-serine dehydratase activity. The invention also relates to microorganisms used in methods for producing L-serine.

3 Claims, 3 Drawing Sheets

OTHER PUBLICATIONS

K. Kubota et al; Fermentative production of L-serine; J. Gen. Appl. Microbiol., 17, 167-168 (1971).

K. Kubota et al; Fermentative production of L-serine; J. Gen. Appl. Microbiol., 18, 365-375 (1972).

K. Kubota et al; Production of L-Serine from . . . ; Jour. Of Fermentation and Bioengineering; vol. 67, 387-390, 1989.

* cited by examiner

NUCLEOTIDE SEQUENCES OF CORYNEFORM BACTERIA CODED FOR PROTEINS PARTICIPATING IN L-SERINE METABOLISM AND METHOD FOR MICROBIAL PRODUCTION OF L-SERINE

CROSS REFERENCE TO RELATED APPLICATIONS

This application is a divisional of U.S. patent application Ser. No. 10/549,262 filed 10 May 2006, which is the US National Phase of PCT/DE 2004/000248 filed 12 Feb. 2004 and claiming the benefit of the priority of German Patent Application 103 11 399 1 filed 13 Mar. 2003.

FIELD OF THE INVENTION

The invention relates to nucleotide sequences of coryneform bacteria coding for proteins with diminished L-serine dehydratase activity and to recombinant microorganisms expressing said proteins and to methods of making L-serine using said microorganisms.

BACKGROUND OF THE INVENTION

The amino acid L-serine has been found to be useful in the food industry, the animal feed industry and pharmaceutical industry as well as in human medicine. It serves as a building block for the synthesis of other industrial valuable products like for example L-tryptophan from indole and L-serine.

It is known that L-serine can be produced by the fermentation of coryneform bacteria strands. Thus for example a strain of *Corynebacterium glycinophilum* is capable of forming L-serine from glycine and carbohydrates (Kubota K, Kageyama K, Shiro T and Okumura S (1971) Journal of General Applications in Microbiology, 17: 167-168; Kubota K, Kageyama K, Maeyashiki I, Yamada K and Okumura S (1972) Journal of General Applications in Microbiology 18: 365). The enzyme L-serine-hydroxy methyl transferase here participates in the conversion of glycine to L-serine. (Kubota K and Yokozeki K (1989) Journal of Fermentation and Bioengineering, 67(6):387-390. These *corynebacterium glycinophilum* strands have a defective serine dehydrataze which produces undirected mutagenesis (Kubota K (1985) Improved production of L-serine by mutants of *Corynebacterium glycinophilum* with less serine dehydratase activity: Agricultural Biological Chemistry, 49:7-12). This enzymatic activity is (Pyridoxal 5'-Phosphate) dependent and not molecularly characterized. (Kubota K., Yokozeki K, Ozaki H. (1989) Effects of L-serine dehydratase activity on L-serine production by *Corynebacterium glycinophilum* of an examination of the properties of the enzyme. Agric. Biol. Chem. 49:7-12. From U.S. Pat. No. 4,528,273 a method of producing L-serine from glycine is known in which the microorganism serine dehydratase is negative.

Furthermore, L-serine can be produced fermentatively from methanol and glycine with the aid of methylotropic bacteria like for example *Hyphomicorbiium* (Izumi Y, Yoshida T, Miyazaki S S, Mitsunaga T, Ohshiro T, Shiamo M, Miyata A and Tanabe T (1993) Applied Microbiology and Biotechnology, 39: 427-432). In both cases the amino acid glycine must be introduced as a precursor for the formation of the amino acid L-serine.

In addition, coryneform bacteria are known which can produce the L-serine directly from carbohydrates without further addition of precursors.

This is advantageous for industrial scale economical production of L-serine since the L-serine can be made directly from carbohydrates without the expensive addition of precursors, these strands which belong to the family *Corynebacterium glutamicum* for resistance of the L-serine analog serine hydroxamate and -chloroalamin and are obtained by undirected mutagenesis {Yoshida H and Nakamaya K (197) NIHON-Nogli-Kagakukaishi 48: 201-208}.

There are also *brevibacterium flavum* strains known which have because of undirected mutagenesis defects, in the breakdown of L-serine, an unused activity of the serA coded 3-phosphoglycerate dehydrogenase and an overexpression of serB and serC genes deriving from *escherichia coli* (EP0931833A2).

OBJECTS OF THE INVENTION

It is an object of the invention to make available features which will permit improved production of L-serine or metabolic products which derive therefrom like for example tryptophan. It is thus also an object of the invention to provide nucleic acids which code for proteins participating in L-serine metabolism and which by comparison with the proteins derived from the wild type organism show no decomposition of L-serine to pyruvate or a reduced decomposition of L-serine to pyruvate. Further it is an object of the invention to provide an L-serine dehydratase as well as microorganisms with an L-serine dehydrotaze shown to reduce decomposition of L-serine which is also an object of the invention to provide an improved method for the microbial production of L-serine.

SUMMARY OF THE INVENTION

The objects of the invention are achieved by providing A nucleic acid which is replicatable in a microorganism of the family *Corynebacterium* and optionally a recombinant nucleic acid, characterized in that it has a nucleotide sequence coding for L-serine dehydratase which is partially or completely mutated or expressed to a lesser degree than the naturally occurring nucleotide sequence or which is not expressed at all.

The objects of the invention are achieved by further providing a gene structure containing at least one nucleotide sequence as described above having regulatory sequences operatively linked therewith.

The objects of the invention are achieved by further providing a vector containing at least one nucleotide sequence as described above or a gene structure as described above and additional nucleotide sequences for selection, for replication in the host cell or for integration in the host cell genome.

The objects of the invention are achieved by further providing L-serine dehydratase with reduced L-serine dehydratase activity coded with a nucleotide sequence as described above.

The objects of the invention are achieved by further providing a microorganism having a nucleotide sequence which codes for an L-serine dehydratase, which is deleted in whole or in part or is mutated or is expressed to a reduced extent by comparison with the naturally occurring nucleotide sequence or is not expressed at all.

The objects of the invention are achieved by further providing a probe for identifying genes for coding which participate in the biosynthesis of L-serine and that are produced starting with nucleic acids as described above and that contain a suitable marker for detection.

The objects of the invention are achieved by providing a method for the microbial production of L-serine which comprises the steps of:

(a) a genetically altered microorganism is produced in which the nucleic acid in the microorganism coding for the L-serine dehydratase as described above is partially or completely deleted or mutated or expressed to a reduced extent by comparison with the naturally occurring nucleic acid or is not expressed at all, (b) this genetically altered microorganism from step (a) is used for microbial production, and (c) the L-serine formed is isolated from the culture medium.

With the nucleic acids and polypeptides according to the invention it is possible to produce an L-serine dehydratase such that there is a reduced decomposition of L-serine or no longer any decomposition of L-serine. Furthermore, it is possible to provide microorganisms and a method by which L-serine production can be obtained with higher yield by comparison with hitherto known microbial methods. According to the invention, in microorganisms of the corynebacterium family, replicatable and optionally recombinant nucleic acid is provided with a nucliatide sequence coding for the L-serine dehydratase, hereinafter referred to also as SDA, which is partially or completely deleted or mutated or is expressed to a reduced extent by comparison with the naturally occurring nucliatide sequence or is not expressed at all.

The subject of the invention is, further, the provision of nucleic acids whose sdaA gene sequence, partially or completely deleted or mutated or has, relative to the naturally available nucleotide sequence reduced expression or which does not express at all. For example the nucleic acid with a nucleotide sequence according to SEQ ID No 1 can have its nucleotide from position 506 to position 918, partly or completely deleted or mutated or an allele, homologue or derivative of this nucleotide sequence or a nucleotide sequence which hybridizes therewith have been found to be advantageous. In addition, it has been found to be advantageous for the deletion or mutation of the cysteine-containing sequence required for forming the iron-sulfur clusters Hofmeister et al., (1994) Iron-sulfur cluster-containing L-serine dehydratase from *Peptostreptococcus asaccharolyticus*: correlation of the cluster type with enzymatic activity. FEBS Letters 351: 416-418), has been found to be advantageous.

The wild type L-serine-dehydratase (sdaA) sequence is generally known and can be obtained by the artisan from the known data bank (NCBI Accession Nr. AP005279) or from the attached sequence protocol according to SEQ ID No. 1.

The complete deletion of the L-serine dehydratase (sdaA) gene can be achieved for example by directed recombinant DNA techniques. Suitable methods for this purpose are found in Schafer et al. (Gene (1994) 145: 69-73) or also Link et al. (Journal of Bacteriology (1998) 179: 6228-6237). Furthermore, only a part of the gene can be deleted or also mutated fragments of the L-serine dehydratase gene can be formed by replacement. By deletion or replacement it is possible to achieve a loss or a reduction in the L-serine dehydratase activity. An example of such mutant is *C. Glutamicum* strain ATCC133032ΔsdaA which has a deletion in the sdaA gene.

To limit the expression of the sdaA gene or achieve reduced expression, for example, the promoter and regulatory regions which are located upstream of the structural gene can be mutated. In a similar manner, expression regulatory cassettes can be built onto the structural gene, upstream thereof. By regulatable promoters it is additionally possible to reduce the expression in the course of formutative L-serine formation. It is also possible to provide a regulation of the translation in which for example the stability of the m-RNA is reduced. Furthermore, genes can be used which code for the corresponding enzyme with reduced activity. Alternatively, furthermore, a reduced expression of the L-serine dehydratase gene can be achieved by varying the medium composition and culture condition. Guides thereto for the artisan can be found among others in Martin et al. (Bio/Technology 5, 137-146 (1987)), by Guerrero et al. (Gene 138, 35-41 (1994)), Tsuchiya and Morinaga (Bio/Technology 6, 428-430 (1988)), Eikmanns et al. (Gene 102, 93-98 (1991)), in the European Patents EPS 0 472 869, U.S. Pat. No. 4,601,893, Schwarzer and Puhler (Bio/Technology 9, 84-87 (1991)), Reinscheid et al. (Applied and Environmental Microbiology 60, 126-132 (1994), LaBarre et al. (Journal of Bacteriology 175, 1001-1007 (1993)) and in patent application WO 96/15246.

The nucleic acids according to the invention are characterized that they can be isolated from the corynebacterium or brevibacterium family and especially preferably from *corynebacterium glutamicum*. Examples of the coryneform bacteria wild types, from this parental line are as follows: *corynebacterium acetoacidophilum* ATCC 13870; *Corynebacterium acetoglutamicum* ATCC 15806; *Corynebacterium callunae* ATCC 15991; *Corynebacterium glutamicum* ATCC 13032; *Brevibacterium divaricatum* ATCC 14020; *Brevibacteriium lactofermentum* ATCC 13869; *Corynebacterium lilium* ATCC 15990; *Brevibacteriiunm flavum* ATCC 14067; *Corynebacterium melassecola* ATCC 17965; *Brevibacterium saccharolyticum* ATCC 14066; *Brevibacterium immariophilum* ATCC 14068; *Brevibacterium roseum* ATCC 13825; *Brevibacterium thiogenitalis* ATCC 19240; *Microbacterium ammoniaphilum* ATCC 15354.

Examples for the production of mutants or production strands suitable for the production of L-serine are organisms from the group of *Arthrobacter, Pseudomonas, Nocardia, Methylobacterium, Hyphomycrobium, Alcaligenes* or *Klebsiella*. The present invention is characterized more particularly by the naming of the aformentioned bacterial strains but should not be considered limited thereto.

By a "nucleic acid" or a "nucleic acid fragment" there is to be only, in accordance with the invention, a polymer of RNA or DNA which can be single stranded or double stranded and can have optional natural chemically synthesized, modified or artificial nucleotides. The term "DNA polymer" includes in this case also genomic DNA, cDNA or mixtures thereof.

Under "alleles" are to be understood functional equivalents in accordance with the invention, that is substantially similarly effective nucleotide sequences. Functionally equivalent sequences are such sequences which, in spite of different nucleotide sequences, for example because of the degeneration of the genetic code, still retained the desired function. Functional equivalents thus encompass naturally occurring variants of the sequences described therein as well as synthetic nucleotide sequences, for example those obtained by chemical synthesis and optionally nucleotide sequences matched to the code on utilization of the host organism.

A functional equivalent is to be understood to include especially natural or synthetic mutations of the original altered sequence which retain the desired function. Mutations include substitutions, additions, deletions, replacements or insertions of one or more nucleotide residues. Included here are also sense mutations which in the protein plane can result for example from the replacement of conserved amino acids which, however, do not lead to any basic alteration in the activity of the protein and thus can be considered functionally neutral. This includes modifications of the nucleotide sequence which involve in the protein plane the N-terminus of a protein without, however, affecting significantly the function of these proteins.

With the present invention, such nucleotide sequences are encompassed which, by modification of the nucleotide sequences can result in corresponding derivatives. The target of such modification can, for example, be a restriction of the coding sequence contained therein or for example also the insertion of further restriction enzymes cutting sites.

In addition, the present invention includes artificial DNA sequences as long as they, as described above, afford the desired characteristics. Such artificial DNA sequences can for example, be those obtained by reverse translation from proteins established by means of computer supported programming (molecular modeling) or by in vitro selection. Especially suitable are coded DNA sequences which, by reverse translation, can produce a polypeptide sequence which has a specific code on utilization for the host organism. The specific code on utilization can be easily determined by molecular genetic methods common in the art using computer evaluations from other previously known genes of the organism to be transformed.

"Homologous sequences" are to be understood in accordance with the invention to be those sequences which are complementary to the nucleotide sequences according to the invention and/or such sequences which can hybridize with them. The hybridizing sequences include, according to the invention, substantially similar nucleotide sequences from the group of DNA or RNA which under stringent conditions known per se undergo a specific interaction (binding) of the aforementioned nucleotide sequences. In this category are to be counted also short nucleotide sequences with a length of for example 10 to 30 and preferably 12 to 15 nucleotides. These include according to the invention among others, also so-called primers or probes.

Included in the invention are also the coded regions (structure genes) and preceding (5' or upstream) sequence regions and/or following (3' or downstream) sequence regions. Especially in this category are sequence regions with regulatory functions. They can influence the transcription, the RNA stability or RNA processing as well as the translation. Example of regulatory sequences are, among others, promoters, enhancers, operators, terminators or translation amplifiers.

The subject of the invention is in addition a gene structure containing at least one of the aforedescribed nucleotide sequences and regulatory sequences operatively linked therewith which control expression of the coded sequences in the host cell.

In addition the present invention relates to a vector containing a nucleotide sequence of the aforedescribed kind with its regulator nucleotide sequence operatively linked thereto as well as additional nucleotide sequences for the selection of host cells capable of effecting transformation, for replication within the host cell or for integration in the corresponding host cell genome. In addition, the vector according to the invention can contain a genome structure of the aforedescribed type. Suitable vectors are thus which replicate in coryneform bacteria like for example pZ1 (Menkel E, Thierbach G, Eggeling L, Sahm H., 1989, *Appl Environ Microbiol* 55(3): 684-688), pEKEx2 (Eikmanns et al., Gene 102: 93-98 (1991), or pXMJ19 (Jacoby M., Burkovski A (1999) Construction and application of new *Corynebacterium glutamicum* vectors, Biotechnol. Technique 13:437-441). Other plasmid vectors can be used in the same manner. These identifications are however not limiting for the present invention.

Utilizing the nucleic acid sequence according to the invention, corresponding probes or primers can be synthesized and used, for example, to amplify and isolate analogous genes from other microorganisms, preferably coryneform bacteria, for example with the aid of the PCR technique.

The subject matter of the present invention is thus also a probe for identifying and/or isolating genes coded for proteins participating in the biosynthesis of L-serine, whereby these probes are produced starting from the nucleic acid sequences according to the invention of the aforedescribed type and which contain a suitable marker for detection. In the probe, a partial segment of the sequences according to the invention, for example a conserved region, can be used which for example has a length of 10 to 30 or preferably 12 to 15 nucleotides and under stringent conditions can hybridize with homologous nitride sequences. Numerous suitable markers are known from the literature. The skilled worker in the art can be guided thereto by among others the Handbook of Gait: Oligonucleotide synthesis: a practical approach (IRL Press, Oxford, UK, 1984) and Newton and Graham: PCR (Spektrum Akademischer Verlag, Heidelberg, Deutschland, 1994) or for example, the Handbook "The DIG System Users Guide for Filter Hybridization" the Firma Roche Diagnostics (Mannheim, Deutschland) and Liebl et al. (International Journal of Systematic Bacteriology (1991) 41: 255:260).

The subject matter of the present invention includes, further, an L-serine dehydratase which shows reduced L-serine decomposition by comparison with the wild type L-serine dehydratase and which is coded by a nucleic acid sequence according to the invention or its variants of the aforedescribed type. The present invention thus includes an L-serine dehydratase or an L-serine dehydratase mutant with an amino acid sequence in accordance with sequence ID No. 2 whose amino acids from position 135 to position 274, for example, as a consequence of a directed mutagenesis in the DNA plane, is altered or is a modified form of this polypeptide sequence or an isoform thereof or a mixture thereof. By "altered" in the framework of the present invention one should understand that complete or partial removal or replacement of the amino acids from position 135 to position 274 is contemplated.

Under isoforms we understand enzymes with the same or comparable substrate specificity and effectiveness specificity but which differ with respect to the primary structure.

Under modified forms are to be understood enzymes according to the invention with changes in the sequence, for example, at the N-terminus or C-terminus of the polypeptide or in the regions of the conserved amino acids without however negatively affecting the function of the enzyme. These changes can be in the form of amino acid replacement in accordance with methods known per se.

The polypeptides according to the invention are characterized by the fact that they derive from coryneform bacteria and preferably of the corynebacterium or brevibacterium family and especially of the *corynebacterium glutamicum* or *brevibacterium* types and especially preferably derived from *corynebacterium glutamicum*. Examples of the coryneform bacteria of the strain culture in the wild type are for instance *Corynebacterium acetoacidophilum* ATCC 13870; *Corynebacterium acetoglutamicum* ATCC 15806; *Corynebacterium callunae* ATCC 15991; *Corynebacterium glutamicum* AT CC 13032; *Brevibacterium divaricatum* ATCC 14020; *Brevibacterium lactofermentum* ATCC 13869; *Corynebacterium lilium* ATCC 15990; *Brevibacterium flavum* ATCC 14067; *Corynebacterium melassecola* ATCC 17965; *Brevibacterium saccharolyticum* ATCC 14066; *Brevibacteriium immariophilum* ATCC 14068; *Brevibacterium roseum* ATCC 13825;

*Brevibacterium thiogenitalis* ATCC 19240; *Microbacterium ammoniaphilum* ATCC 15354;

Examples of mutants or production strands suitable for the production of L-serine are organisms from the group of *arthrobacter, pseudomonas, nocardia, methylobacterium, hyphomycrobium, alcaligenes* or *klebsiella*. The present invention has been characterized by listing the aforementioned bacteria strands but this list should not be considered limiting of the invention.

The present invention comprises, further, a genetically altered microorganism characterized in that it contains a nucleotide sequence coding for the L-serine dehydratase which is in part or completely deleted or mutated or expressed to a reduced extent by comparison with the naturally occurring nucleotide sequence or which is not exposed at all.

The invention comprises further a microorganism which is characterized in that the sdaA gene is partially or completely deleted or mutated or which is expressed to a reduced extent by comparison with the naturally occurring sdaA gene or which is not expressed at all. The invention encompasses as well a genetically altered microorganism containing or in replicatable form a gene structure by a vector of the aforedescribed type.

The subject of the present invention is moreover also a genetically modified microorganism containing a polypeptide according to the invention of the aforedescribed type and which in comparison to the corresponding genetically unmodified microorganism effects reduced or no L-serine decomposition.

A microorganism which, according to the invention has been genetically modified is characterized further in that it is a coryneform bacterium, preferably of the family corynebacterium or brevibacterium and especially preferably of the species *corynebacterium glutamicum* or *brevibacterium flavum*.

Basically the genes can, using methods known pe se like for example the polymerase chain reaction (PCR) be amplified by the aid of short synthetic nucleotide sequences (primers) and then isolated. The production of the primers used can be effected generally based upon known gene sequences from existing homologies in conserved regions of the gene and/or taking into consideration the GC content of the DNA of the microorganism investigated.

A further procedure for isolating coding nucleotide sequences is the complementation of so-called defect mutants of the organism to be investigated which at least phenotypically show a function drop in the activity of the gene investigated or the corresponding protein. Under a complementation is to be understood the preservation of the gene defect of the mutant and the substantial reproduction of the original configuration before mutagenesis which can be achieved by the insertion of functional genes or gene fragments from the microorganism to be investigated. A classical mutagenesis process for producing defect mutants or mutants with a reduced L-serine dehydratase or an L-serine dehydratase which has been shut down is for example the treatment of the bacteria cell with chemicals like for example N-Methyl-N-Nitro-N-Nirosoguanidine or the use of UV radiation. Such methods of mutation resolution are generally known and can be found among others in Miller (A Short Course in Bacterial Genetics, A Laboratory Manual and Handbook for *Escherichia coli* and Related Bacteria (Cold Spring Harbor Laboratory Press, 1992)) or the Handbook "Manual of Methods for General Bacteriology" of the American Society for Bacteriology (Washington D.C., USA, 1981).

The present invention relates moreover to a method for the microbial production of L-serine whereby the nucleic acids in the microorganisms which code for the L-serine dehydratase in part or completely are deleted or mutated or expressed to a lesser extent or practically not at all by comparison with the naturally available nucleic acids, using these genetically altered microorganisms for the microbial production of L-serine, and isolating the correspondingly formed L-serine from the culture medium.

The genetically altered microorganisms produced in accordance with the invention can be used for the purpose of culturing L-serine in continuous cultures or discontinuously in batch processes (set cultivation) or in a fed batch process or a repeated fed batch process. A collection of known cultivation methods can be found in the textbook of Chmiel (Bioprozesstechnik 1. Einfuhrung in die Bioverfahrensechnik (Gustav Fischer Verlag, Stuttgart, 1991)) or in the Storhas (Bioreaktoren und periphere Einrichtungen (Vieweg Verlag, Braunschweig/Wiesbaden, 1994).

The culture medium used must be sufficient to suitably satisfy the requirements of the respective strain. Descriptions of culture media for various microorganisms can be found in the handbook "Manual of Methods for General Bacteriology" der American Society for Bacteriology" der American Society for baceriology (Washington D.C., USA, 1981) as carbon sources, sugars and carbohydrates like for example glucose, saccharose, lactose, fructose, maltose, molasses, starch and cellulose can be used, oils and fats like for example soy oil, soy flour oil, peanut oil, cocoanut fats can be used, fatty acids like for example palmitic acid, stearic acid and linolaic acids can be used, alcohols like for example glycerine and ethanol can be used and organic acids like for example acetic acid can be used. These substances can be employed individually or as mixtures as nitrogen sources, organic nitrogen containing compounds like peptones, yeast extract, meat extract, malt extract, corn spring water, soybean meal and urea, or inorganic compounds like ammonium sulfate, ammonium chloride ammonium phosphate, ammonium carbonate and ammonium nitride are used. The nitrogen sources can be used individually or as mixtures. As phosphorous sources, phosphoric acid, potassium dihydrogen phosphate or dipotassium phosphate or the corresponding sodium-containing salts are used. The culture medium must contain further salts of metal like for example magnesium sulfate or iron sulfate which are required for growth. Finally essential nutrients like amino acids and vitamins are added to the above-mentioned substances. The culture medium can in addition have suitable precursors added to it. The additives can be introduced into the culture in the form of one time addition or can be fed to the culture suitably during cultivation. For pH control of the culture basic compounds like sodium hydroxide, potassium hydroxide, ammonia or aqueous ammonia can be used or acid compounds like phosphoric acid or sulfuric acid can be used in a suitable way. For control of foaming, antifoaming agents like for example fatty acid polyglycol esters can be used. To maintain the stability of plasmids suitable selectively effective substances, for example antibiotics can be added to the medium. To maintain the aerobic conditions, oxygen or oxygen-containing mixtures like for example air are introduced into the culture. The temperature of the culture is normally between 20° C. and 45° C. and preferably 25° C. to 40° C. The culture is maintained for a duration until L-serine production is a maximum. This duration is normally from 10 hours to 160 hours.

The analysis of the L-serine formation can be carried out by anion exchange chromatography with subsequent ninhydrin derivatization as described by Spackman et al. (Analytical Chemistry, 30 (1958), 1190) or the analysis can be effected by reverse phase HPLC as described by Lindroth et al. (Analytical Chemistry (1979) 51: 1167-1174.

The microorganisms which are the subject of the present invention can produce L-serine from glucose, saccharose, lactose, mannose, fructose, maltose, molasses, starch, cellulose or from glycerine and ethanol. It can use the CORYNEFORM bacteria representatives which have already been described in detail. A selection of the results of the fermentation has been given in Table 1. The genetically altered microorganisms of the invention show a substantially improved L-serine production by comparison with the corresponding nontransformed microorganism (wild type) or the microorganisms which contain only the vector without the gene insert. In a special variation of the present invention it has been shown that C. Glutamicum ATCC 13032ΔpanBCΔsdaA gives rise to at least 4-fold increase in the L-serine accumulation in the medium by comparison with the control strain (Table 1). Through the common overexpression of other genes, which act positively on the L-serine biosynthesis pathway, a 16-fold increase in L-serine production can be achieved.

Amino acid production strains, in accordance with the present invention should be understood to be *corynebacterium glutamicum* strains or homologous microorganisms which are altered by classical and/or molecular genetic methods so that metabolic flow is amplified in the direction of the biosynthesis of amino acids or their derivatives (metabolic engineering). For example, with these amino acid production strains, one or more genes and/or the corresponding enzyme have their regulation altered or are rendered deregulated at different and correspondingly complex regulated key positions in the metabolic pathway. The present invention includes thereby all such already known amino acid production strains preferably of the corynebacterium family or homologous organisms. Further, such production strains are encompassed within the invention which the skilled worker in the art will recognize by analogy with other microorganisms, for example, enterobacteria, Bacillaceae or yeast types can be produced by current methods.

DETAILED DESCRIPTION OF THE DRAWINGS

Figure 1:
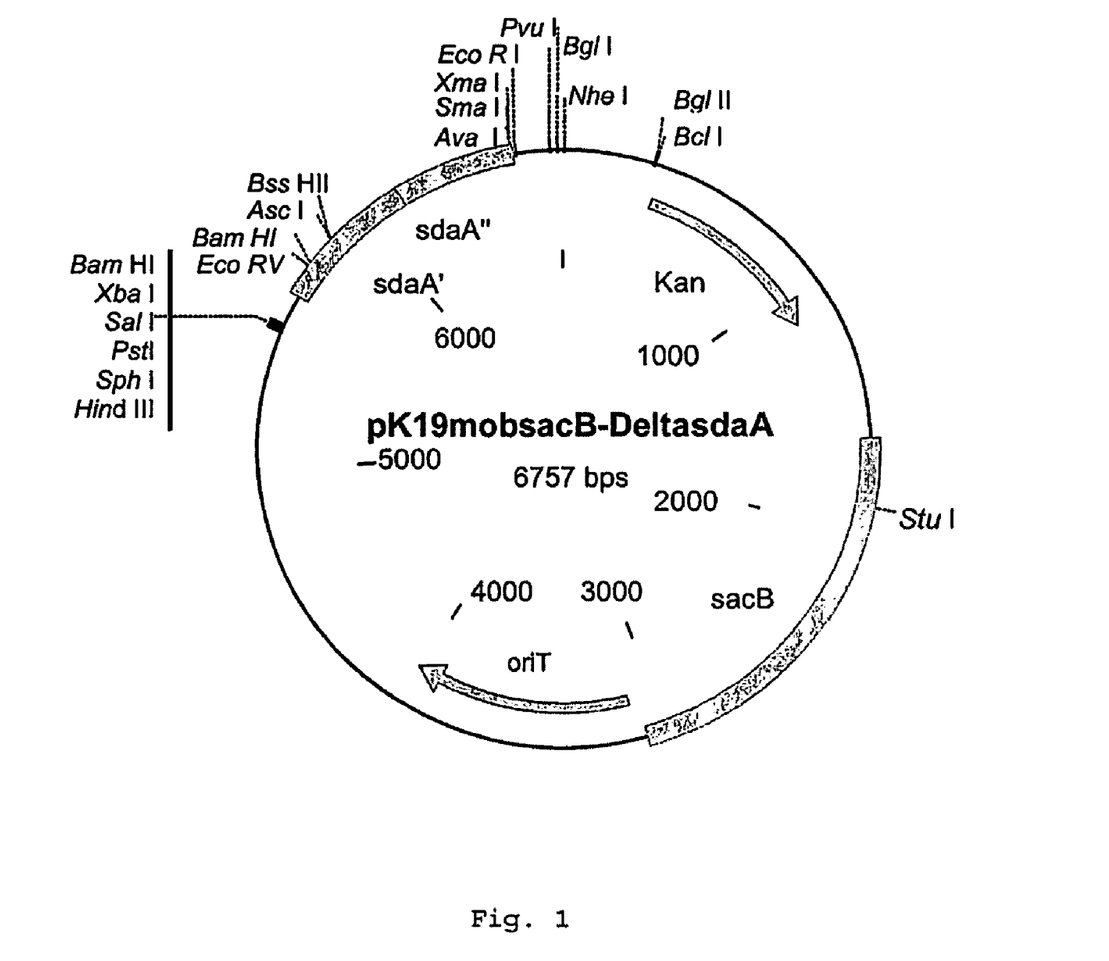
FIGS. 1 and 3 are maps of plasmids which can be used respectively to obtain and to express the polynucleotides according to the present invention and FIG. 2 is a set of graphs showing experimental results with respect to microorganisms transformed with the nucleic acids according to the invention.

FIG. 1 is a map of the integration plasmid pK19mobsacB-DeltasdaA Markings on the outer edge of the plasmid indicate the respective restriction sites. The partition within the circle indicates the following gene:

| | |
|---|---|
| kan | kanamycin resistance |
| sacB | Sucrase |
| OriT | Transfer origin |
| sdA' | 5' n of the sdaA gene |
| sda" | 3' n of the sdaA gene |

Figure 2:
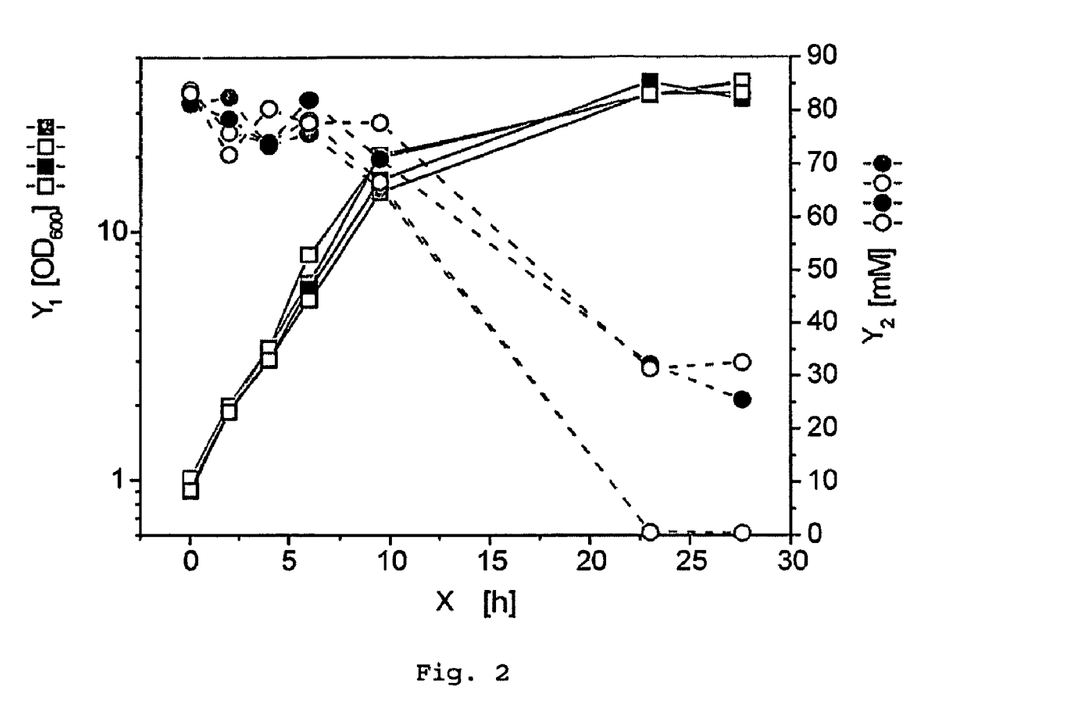

FIG. 2 is a set of graphs showing the ratio between growth (□) and L-serine breakdown (○) of *C. glutamicum* 13032ΔpanBCΔsdaA, clone 1 (□, ○) and *C. glutamicum* 13032ΔpanBCΔsdaA, clone 2 (■, ●) compared with *C. glutamicum* 13032ΔpanBC, clone 1 (□, ○) and *C. glutamicum* 13032ΔpanBC, clone 2 (■, ○). The abscissa X represents the fermentation in hours (h). The ordinate $y_1$ is the growth of the microorganisms measured in terms of optical density at 600 nm. The ordinate $Y_2$ gives the L-serine concentration in mM.

Figure 3:
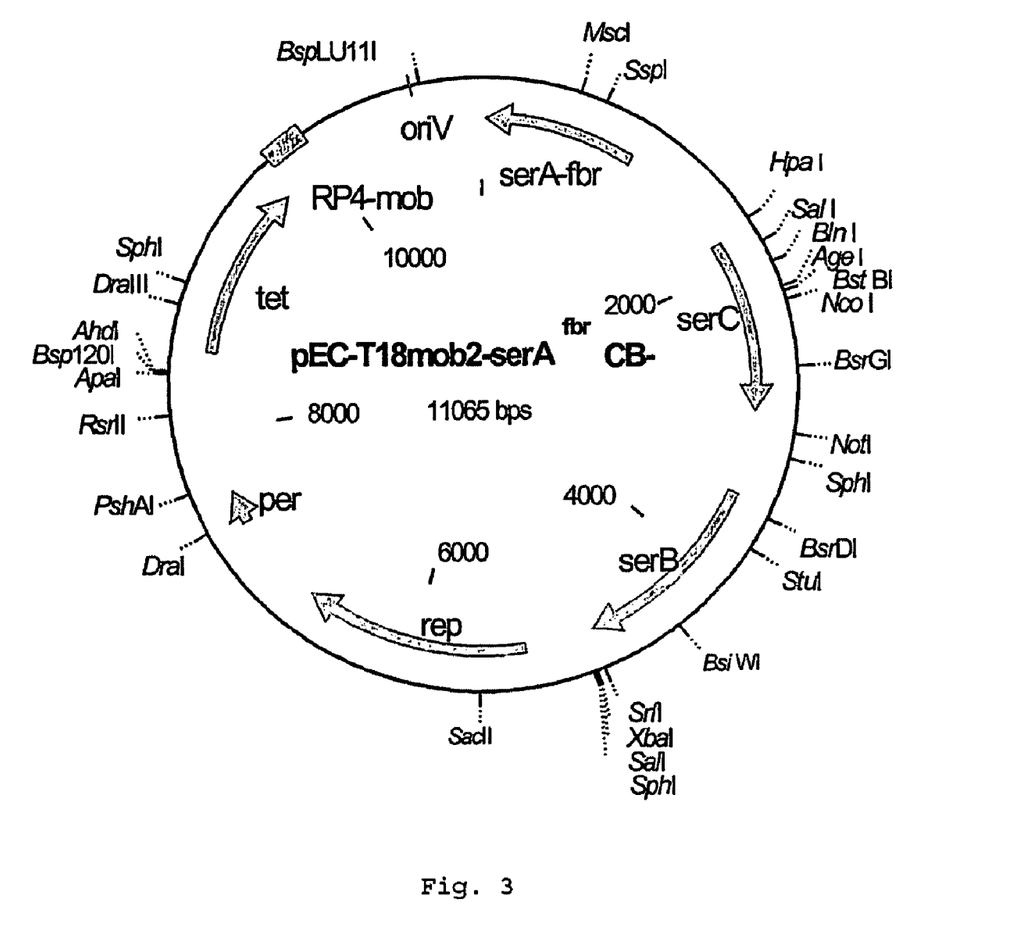

FIG. 3 is a map of the expression plasmid pEC-T18mob2-serA$^{fbr}$CB.
The indicia on the outer edge of the plasmid show the respective restriction sites. The indicia within the circle represent the following genes:

| | |
|---|---|
| SerC | Phosphoserine Transaminase |
| SerB | Phsopserine Phosphatase |
| Rep | Replication origin |
| Per | Partition cell partition gene |
| Tet | Tetracycline resistance gene |
| RP4-mob | Mobilization origin |
| OriV | Source of DNA replication |
| SerA-fbr | 3-phosphoglycerate dehydrogenase |

EXAMPLES

1. The Construction of sdaA-Deletion Mutant of *C. glutamicum* ATCC13032 ΔpanBC

The starting point was *Corynebacterium glutamicum* with a nucleotide sequence (Genbank-Accession-Number BAB99038; SEQ-ID-No. 1) whose derivative polypeptide sequence showed 40% identify with the described L-serine dehydratase of *e coli* (NCBI-Accession-Number P1095). By gene protected mutagenesis by the method of Link et al (Link A J, Phillips D, Church G M, Methods for generating precise deletions and insertions in the genome of wild-type *Escherichia coli*: application to open reading frame characterization. J. Bacteriol. 1997 October; 179(20):6228-37) and Schafer et al. (Gene 145: 69-73 (1994)) the sdaA-gene of *C. glutamicum* was deleted. The following primers we derived from the sdaA corynebacterial sequence (NCBI Accession-Number AP005279):

```
sdaA-1:
                                      (SEQ ID NO: 3)
5'-TCGTGCAACTTCAGACTC-3'
(AP005279 nucleotide 73635-73653);

sdaA-2:
                                      (SEQ ID NO: 4)
5'-CCCATCCACTAAACTTAAACACGTCATAATGAACCCACC-3'
(AP005279 complementary to nucleotide 74121-
74139);

sdaA-3:
                                      (SEQ ID NO: 5)
5'-TGTTTAAGTTTAGTGGATGGGCCGACTAATGGTGCTGCG-3'
(AP005279 complementary to nucleotide 74553-
74571);

sdaA-4:
                                      (SEQ ID NO: 6)
5'-CGGGAAGCCCAAGGTGGT-3'
(AP005279 nucleotide 75044-75062)
```

Primers sdaA-1 and sdaA-2 flank respectively the beginning and the end of the sdaA-3 make available respective complementary linker regions (see relevant text) which enable in a two-stage PCR process (cross over PCR) a deletion of the sdaA gene in vitro. In a first PCR reaction with the chromosomal DNA of *C. glutamicum*, the primer combination sdaA-1 and sdaA-2 as well as sdaA-3 and sdaA-4 are used. The PCR reaction is carried out in 30 cycles in the presence of 200 µm deoxynucleotide triphosphates (dATP, dCTkP, dGTP, dTTP), each with 600 nM of the corresponding oligonucleotide sdaA-1 and sdaA-4 as well as 60 nM of oligonucleotide sdaA-2 and sdaA-3, 100 ng of chromosomal DNA from *Corynebacterium glutamicum* ATCC13032, 1/10 volumes 10-fold of region buffer and 2.6 units of heat stabilized Taq-/Owi-DNA-Polymerase-Mischung mixture (Expand High Fidelity PCR System of Firm of Roche Diagnostics, Mannheim, Deutschland) in a Sthermocycler (PTC-100, M J Research, Inc., Watertown, USA) under the following conditions: 94° C. for 30 seconds, 50° C. for 30 seconds and 72° C. for 40 seconds. The elongation step at 42° C. was extended after 10 cycles by about 5 seconds per cycle. After the PCR reaction, the DNA fragments containing each having a length of 500 bp were isolated with QIAExII Gel extraction kit (Qiagen) in accordance with the requirements of the manufacturer on an 0.8% agarose gel and both fragments were used as templates in the second PCR. As primers the primers sdaA-1 and sdaA-4 were used. This time the reaction was carried out in 35 cycles in the presence of 200 µm deoxynucleotide triphosphates, 600 nM each of the corresponding olegonitrides, 2-mg each of the isolated template DNA from the first PCR, 1/10 volume of 10 fold reaction buffer and 2.6 units of Taq-/Pwo-DNA-Polymerase mixture under the following conditions: 94° C. for 30 seconds, 50° C. for 30 seconds and 72° C. for 80 seconds. Again the elongation after 10 cycles were extended 5 seconds each. After PCR reaction to 1000 bp long DNA fragments which contain the inactive sdaA gene with a 420 bp long central deletion was isolated on a 0.8% agarose gel and cloned, blunt end with the aid of a short clone kit (Amersham Pharmacia Biotech) in the SmaI-restriction site of the inactivation vector pk19mobsacB (Schafer et al Gene 145: 69-73 (1994) which can replicate only in an *e coli* but not in *C. glutamicum*. The obtained plasmid pK19mobsacB_ΔsdaA (FIG. 1) is tested by restriction mapping for correctness. The cloning was effected in the *Escherichia coli* strain DH5αmcr (Grant et al., Proceedings of the National Academy of Sciences of the United States of America USA (1990) 87: 4645-4649).

Then the plasmid is incorporated by electroporation in *C. glutamicum* 13032ΔpanBC (Radmacher E, Vaitsikova A, Burger U, Krumbach K, Sahm H, Eggeling L. Linking central metabolism with increased pathway flux: L-valine accumulated by *Corynebacterium glutamicum*. Appl Environ Microbiol. 2002 68(5):2246-50) and subject to selection with integration of the vector. This strain is pantothenate auxotrophic as a result of the deletion of the pantothenate biosynthesis genes panB and panC and is characterized in that it has an amplified accumulation of pyruvate about 50 mM alanine and 8 mM valine because of the pantothenate limitation. In addition the strain can form about 100 µM L-serine and is suitable as a starting strain for the construction of L-serine producers. It contains canamycine resistant clones of *C. Glutamicum* 13032ΔpanBC by which inactivation vector is integrated in the genome. To allow selection of the excision of the vector, kanamycin-resistant clones are plated out on saccharose containing LB medium (Sambrook et al., Molecular cloning. A laboratory manual (1989) Cold Spring Harbour Laboratory (Press) with 15 g/l Agar, 2% glucose/10% saccharose) and colonies are obtained in which the vector has again been lost as a result of a second recombination event. (Jager et al. 1992, Journal of Bacteriology 174: 5462-5465). Two of these clones whose nucleotides have sdaA genes deleted from positions 506 to 918 are designated and 13032ΔpanBCΔsdaA, clone 1 and 13032ΔpanBCΔsdaA, clone 2 and are used in the further investigations.

2. The Influence of the sdaA Deletion upon L-Serine Decomposition

In the following, a test was made whether the deleted sdaA gene indeed participates in L-serine decomposition. For this purpose a growth experiment was carried out with each of the two clones of the strains *C. glutamicum* 13032ΔpanBCΔsdaA in comparison with strain *C. glutamicum* 13032ΔpanBC on minimal medium (Keilhauser et al., Journal of Bacteriology 175 (1993) 5595-5603) which additionally contains 2% glucose 1 µM pantothenate and 100 mM L-serine. The growth and consumption of L-serine were followed. The results are given in FIG. 2.

The results in FIG. 2 show that the deletion of the sdaA genes results in about 40% reduced decomposition of L-serine.

3. Influence of the Deletion of the sdaA Gene on L-Serine Formation

To test what the influence was of the deletion of the L-serine dehydratase gene upon L-serine formation the strains 13032ΔpanBCΔsdaA (clone 1, clone 2) and 13032ΔpanBC (clone 1, clone 2) with the plasmid pec-T18mob2-sera$^{fbr}$serCserB the plasmid is formed (FIG. 3) from the vector pEC-T18mob2 (Tauch, A., Kirchner, O., Loffler, B., Gotker, S., Puhler A., and Kalinowski J. Efficient Electrotransformation of *Corynebacterium* diphtheria with a MiniReplicon Derived from the *Corynebacterium glutamicum* Plasmid pGA1. Curr. Microbiol. 45(5), 362-367 (2002)), of the corynebacterial gene serA$^{fbr}$ (Peters-Wendisch P., Netzer R, Eggeling L. Sahm H. 3-Phosphoglycerate dehydrogenase from *Corynebacterium glutamicum*: the C-terminal domain is not essential for activity but is required for inhibition by L-serine. Appl Microbiol Biotechnol. 2-2 December; 60(4); 437-41) as well as serC and serB (German patent application 100 44 831.3 of 11 Sep. 2000.

After electroporation, the strains 13032ΔpanBCΔsdaApSerA$^{fbr}$CB and 13032ΔpanBCpSerA$^{fbr}$CB were obtained.

For testing L-serine output the two strains 13032ΔpanBCΔsdaApSerA$^{fbr}$CB and 13032ΔpanBCpSerA$^{fbr}$CB are cultivated in complex medium (CgIII with 2% glucose and 5 µg/l tetracycline) and the fermentation medium CGXII (J Bacteriol (1993) 175: 5595-5603), each seeded from the preculture to the medium contained in addition 50 µg/l kanamycin and 1 µM pantothenate. As controls, the two starting strains 13032ΔpanBC and 13032ΔpanBCΔsdaA were cultured in the same manner although the medium did not contain tetracycline. For each at least two independent fermentations were carried out. After culturing for 30 hours at 30° C. of a rotating shaker at 120 RPM, the L-serine quantity accumulated in the medium was determined. The determination of the amino acid concentration was carried out by means of high pressure liquid chromatography (J Chromat (1983) 266: 471-482). The results of the fermentation are shown in Table 1 and indicate that the exclusion of L-serine dehydratase led to a 4-fold increase in the L-serine accumulation in the medium independently of whether the L-serine biosynthesis genes serA$^{fbr}$, serC and serB were overexpressed. The overexpression of the L-serine biosynthesis genes serA$^{fbr}$, serC and serB however resulted in 16 fold increase in L-serine accumulation in the culture supernatent generally. Thus the use of the constructed and described deletion mutant ΔsdaA resulted in a method which improved the L-serine formation decisively.

Table 1: Accumulation of L-serine in the culture supernatent of *Corynebacterium glutamicum* 13032ΔpanBC and 13032ΔpanBCΔsdaA after expression of the genes serA$^{fbr}$, serC and serB

| Strain | OD$_{600}$ | L-Serine [mM] |
| --- | --- | --- |
| 13032ΔpanBC | 40 | 0.1 |
| 13032ΔpanBCΔsdaA | 42 | 0.4 |
| 13032ΔpanBCpserA$^{fbr}$CB | 30 | 1.6 |
| 13032ΔpanBCΔsdaApserA$^{fbr}$CB | 30 | 6.6 |

4. Determination of the L-Serine Dehydratase Activity

For determining the L-serine dehydratase activity the wild type strands WT pXMJ19 (Jacoby M., Burkovski A (1999) Construction and application of new *Corynebacterium glutamicum* vectors. Biotechnol. Technique 13:437-441), overexpression strand WT pXMJ19_sdA and the deletion strands ΔsdaA pXMJ19 were cultured in CgXII minimal medium as in Keilhauer et al., (1993). The medium contained 30 mg/l protocatechuic acid, 100 mM glucose and 100 mM L-serine. The cells were cultivated in the presence of 1 mM Isopropyl-beta-D-thiogalactopyranoside and in the exponential growth phase at an optical density of 6-8, measured by a Pharmacia Biotech ultrospec 3000 spectral photometer were harvested. They were then centrifuged for 10 minutes at 4500 rpm and 4° C., suspended in 50 mM N-2-Hydroxyethylpiperazin-N'-2-ethansulfonic acid buffer (pH 8.0) and centrifuged again. Thereafter the cells were taken up in 50 mM N-2-Hydroxyethylpiperazin-N'-2-ethansulfonicacid buffer (pH 8.0), 1 mM FeSO$_4$ and 10 mM Diothiothreitol. The cell breakdown was effected by means of ultrasonic treatment (Branson sonifier 250; duty cycle 25%, output control 2.5, 10 minutes) on ice.

To determine the L-serine dehydratase activity the reaction set contained 50 mM N-2-Hydroxyethylpiperazin-N'-2-ethansulfonic acid buffer (pH 8.0), 10 mM Dithiothreitol and 10-100 μl new extract. The detection of the pyruvate formation from the serine was effected as described (Ohmori et al., 1991). The reaction was started by adding 50 mM L-serine and after 10 minutes was stopped by the addition of 1.2-Diamino-4.5-dimethoxybenzene reagent in a ratio of 1:1. The reagent, as described in Ohmori et al 1991 was comprised of 4 mg 1.2-Diamino-4.5-dimethoxybenzol dissolved in 42.4 ml H$_2$O, 3.5 ml β-Mercaptoethanol and 4.1 ml HCl (37% ig) then incubation was carried out for 2 hours at 102° dry heat.

Detection and quantification of the 2-Hydroxy-6,7-dimethoxy-3-methylquinoxaline derivative produced by the pyruvate carried out by means of high pressure liquid chromatography also as described. (Ohmori et al., 1991). The protein determination in the raw extract followed by means of the Bradford method (Bradford 1976) using the protein assays (The firm Bio-Rad). The specific L-serine dehydratase activity of the two strands are given in Table 2.

Table 2: Specific Activity of the L-Serine Dehydratase in the Strains 13032 WT pXMJ19_sdaA (Overexpressed), 13032 WT pXMJ19 (Wild Type with Empty Vectors) and 13032 ΔsdaA pXMJ19.

| *C. Glutamicum* Strain | spec. Activity [nmol/min*mg] |
| --- | --- |
| 13032 WT pXMJ19__sdaA | 0.221 |
| 13032 WT pXMJ19 | 0.003 |
| 13032 ΔsdaA pXMJ19 | 0 |

We claim:

1. A method for the microbial production of L-serine, which comprises the following steps:
   (a) obtaining a recombinant microorganism having at least one serine biosynthesis sequence selected from the group consisting of serA, serB, and serC and an endogenous nucleotide sequence according to SEQ ID NO:1, which encodes L-serine dehydratase, but whose nucleotide from positions 506 until 918 are completely deleted, so that the endogenous nucleotide sequence which encodes the L-serine dehydratase, but which is modified by the deletion does not encode a protein with L-serine dehydratase activity;
   (b) micro biologically producing L-serine from a carbohydrate by fermentation of the recombinant microorganism obtained according to step (a) in a culture medium; and
   (c) isolating the L-serine from the culture medium, while avoiding decomposition of the L-serine to pyruvate catalyzed by L-serine dehydratase.

2. The method for the microbial production of L-serine defined in claim 1 wherein according to step (a) the recombinant microorganism having at least one serine biosynthesis sequence and an endogenous nucleotide sequence which encodes an L-serine dehydratase, is selected from the group consisting g of *Corynebacterium, Brevibacterium, Arthrobacter, Pseudomonas, Nocardia, Methylobacteria, Hyphomicrobium, Alkaligenes* and *Klebisella*.

3. The method for the microbial production of L-serine defined in claim 1 wherein according to step (b) the carbohydrate is glucose.

* * * * *

```
                       SEQUENCE LISTING

<160> NUMBER OF SEQ ID NOS: 6

<210> SEQ ID NO 1
<211> LENGTH: 1449
<212> TYPE: DNA
<213> ORGANISM: Corynebacterium glutamicum

<400> SEQUENCE: 1
tcgtgcaact tcagactctt acggaggcga tggaccaaaa acaactacaa tcaagcagat      60
caccttgtac accaccatag aaaaggccca ccctcagcca tggctatcag tgttgttgat     120
ctatttagca tcggtatcgg accatcatcc tcacataccg tcggcccat  gagagccgcc     180 ctcacgtata tctctgaatt tcccagctcg catgtcgata tcacgttgca cggatccctt     240
gccgccaccg gtaaaggcca ctgcactgac cgggcggtat tactgggtct ggtgggatgg     300
gaaccaacga tagttcccat tgatgctgca ccctcacccg gcgcgccgat tcctgcgaaa     360
ggttctgtga acgggccaaa gggaacggtg tcgtattccc tgacgtttga tcctcatcct     420
cttccagaac accccaatgc cgttaccttt aaaggatcaa ccacaaggac ttatttgtcg     480
gtgggtggtg ggttcattat gacgttggag gatttccgga agctggacga tatcggatca     540
ggtgtgtcaa ccattcatcc agaggcagag gtgccttgtc cttttcagaa gagttcccaa     600
ttactcgcat atggtcgcga ttttgcggag gtcatgaagg ataatgagcg cttaatccac     660
```

-continued

```
ggggatcttg gcacagtgga tgcccatttg gatcgagtgt ggcagattat gcaggagtgc    720
gtggcacaag gcatcgcaac gccgggatt ttaccgggtg ggttgaatgt gcaacgtcgg    780
gcgccgcagg tacacgcgct gattagcaac ggggatacgt gtgagctggg tgctgatctt    840
gatgctgtgg agtgggtgaa tctgtacgcc ttggcggtga atgaagaaaa cgccgctggt    900
ggtcgtgtgg ttactgctcc gactaatggt gctgcgggga ttattccggc ggtgatgcac    960
tatgcgcggg atttttgac aggttttggg gcggagcagg cgcggacgtt tttgtatacc   1020
gcgggtgcgg tgggcatcat cattaaggaa aatgcctcga tctctggcgc ggaggtgggg   1080
tgtcagggtg aggttggttc agcgtccgcg atggcggctg ccgggttgtg tgcagtctta   1140
ggtggttctc cgcaacaggt ggaaaacgcc gcggagattg cgttggagca caatttggga   1200
ttgacgtgcg atccggtggg cgggttagtg cagattccgt gtattgaacg caacgctatt   1260
gctgccatga agtccatcaa tgcggcaagg cttgcccgga ttggtgatgg caacaatcgc   1320
gtgagtttgg atgatgtggt ggtcacgatg gctgccaccg gccgggacat gctgaccaaa   1380
tataaggaaa cgtcccttgg tggtttggca accaccttgg gcttcccggt gtcgatgacg   1440
gagtgttag                                                            1449
```

<210> SEQ ID NO 2
<211> LENGTH: 449
<212> TYPE: PRT
<213> ORGANISM: Corynebacterium glutamicum

<400> SEQUENCE: 2

```
Met Ala Ile Ser Val Val Asp Leu Phe Ser Ile Gly Ile Gly Pro Ser
  1               5                  10                  15
Ser Ser His Thr Val Gly Pro Met Arg Ala Ala Leu Thr Tyr Ile Ser
             20                  25                  30
Glu Phe Pro Ser Ser His Val Asp Ile Thr Leu His Gly Ser Leu Ala
         35                  40                  45
Ala Thr Gly Lys Gly His Cys Thr Asp Arg Ala Val Leu Leu Gly Leu
     50                  55                  60
Val Gly Trp Glu Pro Thr Ile Val Pro Ile Asp Ala Ala Pro Ser Pro
 65                  70                  75                  80
Gly Ala Pro Ile Pro Ala Lys Gly Ser Val Asn Gly Pro Lys Gly Thr
                 85                  90                  95
Val Ser Tyr Ser Leu Thr Phe Asp Pro His Pro Leu Pro Glu His Pro
            100                 105                 110
Asn Ala Val Thr Phe Lys Gly Ser Thr Thr Arg Thr Tyr Leu Ser Val
        115                 120                 125
Gly Gly Gly Phe Ile Met Thr Leu Glu Asp Phe Arg Lys Leu Asp Asp
    130                 135                 140
Ile Gly Ser Gly Val Ser Thr Ile His Pro Glu Ala Glu Val Pro Cys
145                 150                 155                 160
Pro Phe Gln Lys Ser Ser Gln Leu Leu Ala Tyr Gly Arg Asp Phe Ala
                165                 170                 175
Glu Val Met Lys Asp Asn Glu Arg Leu Ile His Gly Asp Leu Gly Thr
            180                 185                 190
Val Asp Ala His Leu Asp Arg Val Trp Gln Ile Met Gln Glu Cys Val
        195                 200                 205
Ala Gln Gly Ile Ala Thr Pro Gly Ile Leu Pro Gly Gly Leu Asn Val
    210                 215                 220
Gln Arg Arg Ala Pro Gln Val His Ala Leu Ile Ser Asn Gly Asp Thr
225                 230                 235                 240
```

```
Cys Glu Leu Gly Ala Asp Leu Asp Ala Val Glu Trp Val Asn Leu Tyr
            245                 250                 255

Ala Leu Ala Val Asn Glu Glu Asn Ala Ala Gly Gly Arg Val Val Thr
            260                 265                 270

Ala Pro Thr Asn Gly Ala Ala Gly Ile Ile Pro Ala Val Met His Tyr
            275                 280                 285

Ala Arg Asp Phe Leu Thr Gly Phe Gly Ala Glu Gln Ala Arg Thr Phe
        290                 295                 300

Leu Tyr Thr Ala Gly Ala Val Gly Ile Ile Lys Glu Asn Ala Ser
305                 310                 315                 320

Ile Ser Gly Ala Glu Val Gly Cys Gln Gly Glu Val Gly Ser Ala Ser
                325                 330                 335

Ala Met Ala Ala Ala Gly Leu Cys Ala Val Leu Gly Gly Ser Pro Gln
                340                 345                 350

Gln Val Glu Asn Ala Ala Glu Ile Ala Leu Glu His Asn Leu Gly Leu
            355                 360                 365

Thr Cys Asp Pro Val Gly Gly Leu Val Gln Ile Pro Cys Ile Glu Arg
        370                 375                 380

Asn Ala Ile Ala Ala Met Lys Ser Ile Asn Ala Ala Arg Leu Ala Arg
385                 390                 395                 400

Ile Gly Asp Gly Asn Asn Arg Val Ser Leu Asp Asp Val Val Thr
                405                 410                 415

Met Ala Ala Thr Gly Arg Asp Met Leu Thr Lys Tyr Lys Glu Thr Ser
                420                 425                 430

Leu Gly Gly Leu Ala Thr Thr Leu Gly Phe Pro Val Ser Met Thr Glu
        435                 440                 445

Cys

<210> SEQ ID NO 3
<211> LENGTH: 18
<212> TYPE: DNA
<213> ORGANISM: Corynebacterium glutamicum

<400> SEQUENCE: 3
tcgtgcaact tcagactc                                                18

<210> SEQ ID NO 4
<211> LENGTH: 39
<212> TYPE: DNA
<213> ORGANISM: Corynebacterium glutamicum

<400> SEQUENCE: 4
cccatccact aaacttaaac acgtcataat gaacccacc                         39

<210> SEQ ID NO 5
<211> LENGTH: 39
<212> TYPE: DNA
<213> ORGANISM: Corynebacterium glutamicum

<400> SEQUENCE: 5
tgtttaagtt tagtggatgg gccgactaat ggtgctgcg                         39

<210> SEQ ID NO 6
<211> LENGTH: 18
<212> TYPE: DNA
<213> ORGANISM: Corynebacterium glutamicum
```

```
<400> SEQUENCE: 6
cgggaagccc aaggtggt                                                   18
```